United States Patent [19]

Paluch

[11] 4,007,737
[45] Feb. 15, 1977

[54] ANESTHESIA BREATHING SYSTEM

[76] Inventor: Bernard R. Paluch, 1607 E. Cedar Lane, Mount Prospect, Ill. 60056

[22] Filed: Apr. 7, 1975

[21] Appl. No.: 565,536

Related U.S. Application Data

[63] Continuation of Ser. No. 437,033, Jan. 28, 1974, abandoned.

[52] U.S. Cl. .............................................. 128/188
[51] Int. Cl.² ........................................ A61M 17/00
[58] Field of Search .............. 128/188, 191 R, 201, 128/202, 203, 142, 142.2, 142.3, 145 R, 145 A, 145.5, 145.8, 212; 138/114

[56] References Cited

UNITED STATES PATENTS

| | | | |
|---|---|---|---|
| 1,276,752 | 8/1918 | Goodall | 138/114 |
| 1,999,086 | 4/1935 | Claudius | 128/191 R |
| 2,868,198 | 1/1959 | Brooke | 128/188 |
| 3,110,754 | 11/1963 | Witort et al. | 138/114 |
| 3,473,529 | 10/1969 | Wallace | 128/145.7 |
| 3,548,822 | 12/1970 | Seeler et al. | 128/145.7 |
| 3,814,091 | 6/1974 | Henkin | 128/188 |
| 3,815,596 | 6/1974 | Keener et al. | 128/188 |
| 3,865,106 | 2/1975 | Paluch | 128/145.8 |

FOREIGN PATENTS OR APPLICATIONS

| | | | |
|---|---|---|---|
| 520,342 | 2/1921 | France | 128/191 R |
| 146,850 | 9/1921 | United Kingdom | 128/191 R |

*Primary Examiner*—Robert W. Michell
*Assistant Examiner*—Henry J. Recla
*Attorney, Agent, or Firm*—Dominik, Knechtel, Godula & Demeur

[57] ABSTRACT

There is disclosed an anesthesia breathing system which is interconnected between a source of gas, such as an oxygen or an anesthesia administration system, or both, and a patient supported inhalation-exhalation means such as a face mask or the like, which includes concentrically oriented double tubular inhalation and exhalation lines having one of the tubes positioned interiorly of the other tube, spacer means for supporting and maintaining the concentrically oriented tubes and spaced in relatively fixed spacial relation, first uni-directional valve means carried adjacent one end of the tube system and positioned adjacent to the patient supported inhalation-exhalation means to control gas flow through the inhalation tube and second unidirectional valve means adjacent to the first unidirectional valve means to control gas flow through the exhalation tube, such that the double tubular inhalation-exhalation line functions as a heat exchanger to warm the gases as they travel to the patient while at the same time permitting gas flow in the respective lines in one direction only.

10 Claims, 5 Drawing Figures

ANESTHESIA BREATHING SYSTEM

CROSS REFERENCE TO RELATED APPLICATION

This is a continuation of a parent application Ser. No. 437,033, filed on Jan. 28, 1974, now abandoned, in the name of Bernard R. Paluch for ANESTHESIA BREATHING SYSTEM.

BACKGROUND OF THE INVENTION

The present invention relates to an anesthesia breathing circuit and/or system which is useful in either a closed or a semi-closed anesthetic supply system and functions to simplify the overall system while at the same time introducing certain efficiencies and economies of manufacture.

Generally, in the practice in inhalation anesthesia administration, a system is frequently employed wherein a patient undergoing anesthesia rebreathes all or part of the exhaled gases. The inhaled and exhaled gases generally are contained in a circuit which is either closed or semi-closed, a closed circuit preventing any significant amount of gas to leave the circuit while a semi-closed system allows a portion of the gas to escape, usually into the atmosphere. In both systems, the exhalation gases, including carbon dioxide as well as the anesthetic gases are generally directed to a filter system which removes the carbon dioxide and then reintroduces the remaining gases along with additional new gases back into the inhalation portion of the system. In general, the circuit consists of the anesthesia machine, valving to establish unidirectional flow for the gases, a relief or pop-off valve, a carbon dioxide removal device, otherwise known as an absorber, a breathing bag, breathing tubes or conduits for carrying the gas to and from the patient, and a face mask or endotracheal tube.

With respect to those circuits presently known in the art, it is the common practice to employ a separate inhalation tube and a separate exhalation tube, which are each separately connected to the anesthesia machine, and also separately connected to the patient's face mask. By employing unidirectional valves, exhaled gases will mostly enter the exhalation tube, whereas inhaled gases will mostly enter through the inhalation tube, the unidirectional flow valves functioning to prevent the gases from intermixing between the two tube lines. For example, a recent U.S. Pat. No. 3,721,239 discloses an anesthetic gas exhaust system which shows a system of the general type discussed above, having both an inhalation line and an exhalation line connected to an anesthetic supply system at one end, and to the patient face mask at the opposed end. While many recent additions and modifications have been proposed, most of these improvements have dealt with the utilization of materials to allow a single patient disposable application for antiseptic purposes, however, major components of this system have not basically changed. As a result, the various drawbacks which are inherent in such circuits have remained and have merely been accommodated by the majority of the modifications and improvements made in the field.

Exemplary of such drawbacks is the two tubular system, presently employed. Generally, such anesthesia systems include an inhalation line, which interconnects between the anesthesia supply equipment and the patient's face mask, or other patient supported inhalation-exhalation means, and a separate exhalation tube which again interconnects between the patient's face mask or other such device, and some type of purification equipment such as a carbon dioxide absorber. The provision of a two tubular system presents many difficulties, including the accumulation of water within the tubing resulting from condensation from the gases passing through the tubing; the increased danger of bacterial growth in the tubing especially in the presence of accumulated water of condensation; the loss of heat from the gas as it travels down the inhalation line prior to inhalation by the patient; the requirement or necessity for taping or otherwise supporting the tubes, by taping the same to the patient, or the surgical table in order to support the tubes and minimize entanglements; and it is apparent that some degree of manipulative skill is necessary in order to properly connect the tubes. Another drawback, which has been incorporated into the present systems, relates to the location of the unidirectional flow valves at a point somewhat spaced from the patient, or the patient's face mask, that is at the anesthesia machine. The inherent disadvantage to this structure is the fact that there is created a great deal of space for exhaled gas to accumulate or to reside such that a portion thereof may be inhaled during the next inspiration. This results in the inhalation of gas with a higher than desirable concentration of carbon dioxide.

SUMMARY OF THE INVENTION

The present invention is directed towards an anesthesia breathing system, having a concentrically oriented double tubular inhalation and exhalation line, wherein one of the tubes is positioned interiorly of the other two tubes, and including spacer means for supporting and maintaining the concentrically oriented tubes and spaced in relative spacial relation and further including unidirectional valves positioned adjacent the patient receiving portions of the tubing such that one unidirectional flow valve will control the flow of gas from the patient into the exhalation line, while the other valve will control the flow of gas from the anesthesia supply equipment into the patient. The structure of the present invention provides an anesthesia breathing system which is simplified in construction, provides ease of manipulative skill, and substantially eliminates the problem of the gases cooling during travel down the inhalation line prior to entry into the patient without any additional heat source.

It is therefore the principal object of the invention to provide an anesthesia breathing system of the type including at least two concentrically oriented tubular inhalation and exhalation lines having one of the tubes positioned interiorly of the other tubes, spacer means for supporting and maintaining the tubes in spaced and relatively fixed spacial relation, first and second unidirectional valve means, both valve means carried at the end of the double tubular inhalation and exhalation lines, adjacent to the patient, thereby to control the flow of gas exhaled by the patient as well as the flow of gas supplied into the inhalation line, by the anesthesia equipment.

In connection with the foregoing object, it is another object of this invention to provide a breathing system of the type described wherein the systen further includes a U-shaped adaptor carried at the equipment hook-up end of the line, whereby the double tubular system of the present invention can be adapted to interconnect existing anesthesia gas supply equipment as well as presently existing carbon dioxide absorbers.

In connection with the foregoing object, it is still another object of the invention to provide an anesthesia breathing system wherein each of the two tubes forming the inhalation tube and the exhalation tube are smooth walled in construction, both interiorly and exteriorly, thereby to minimize gas turbulence as gases flow through the tubing, as well as to minimize the condensation of water vapor within the tubes during the inhalation and exhalation cycles, and to further minimize tubing distension under conditions of interior pressure.

Still another object of this invention is to provide a breathing system of the type described wherein at least the unidirectional flow valve controlling the flow of exhaled gas from the patient into the tubing system is positioned immediately adjacent the patient's face mask such that there is a minimum of dead space provided in the system for gases to dwell, thereby decreasing the volume of rebreathed gas and the dangers inherent therewith, to the patient.

Further features of the invention pertain to the particular arrangement of the elements and parts whereby the above-outlined and additional operating features thereof are attained.

The invention, both as to its organization and method of operation, together with further objects and advantages thereof will best be understood by reference to the following specification, taken in connection with the accompanying drawings, in which.

Figure 4:
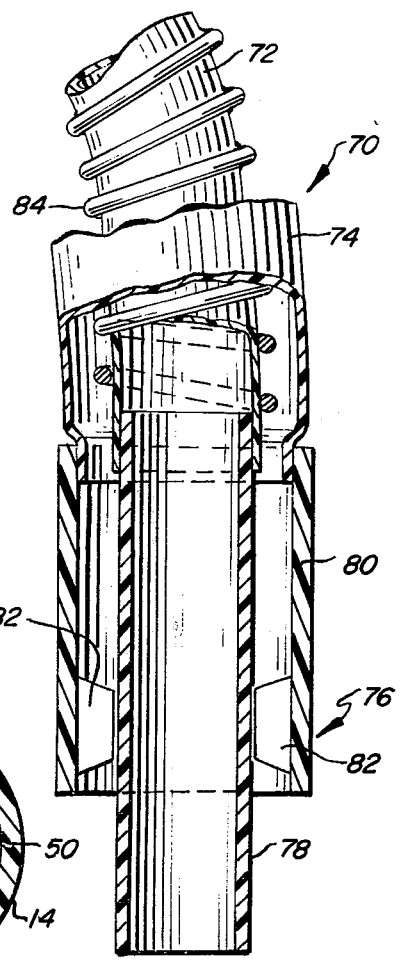
Figure 5:
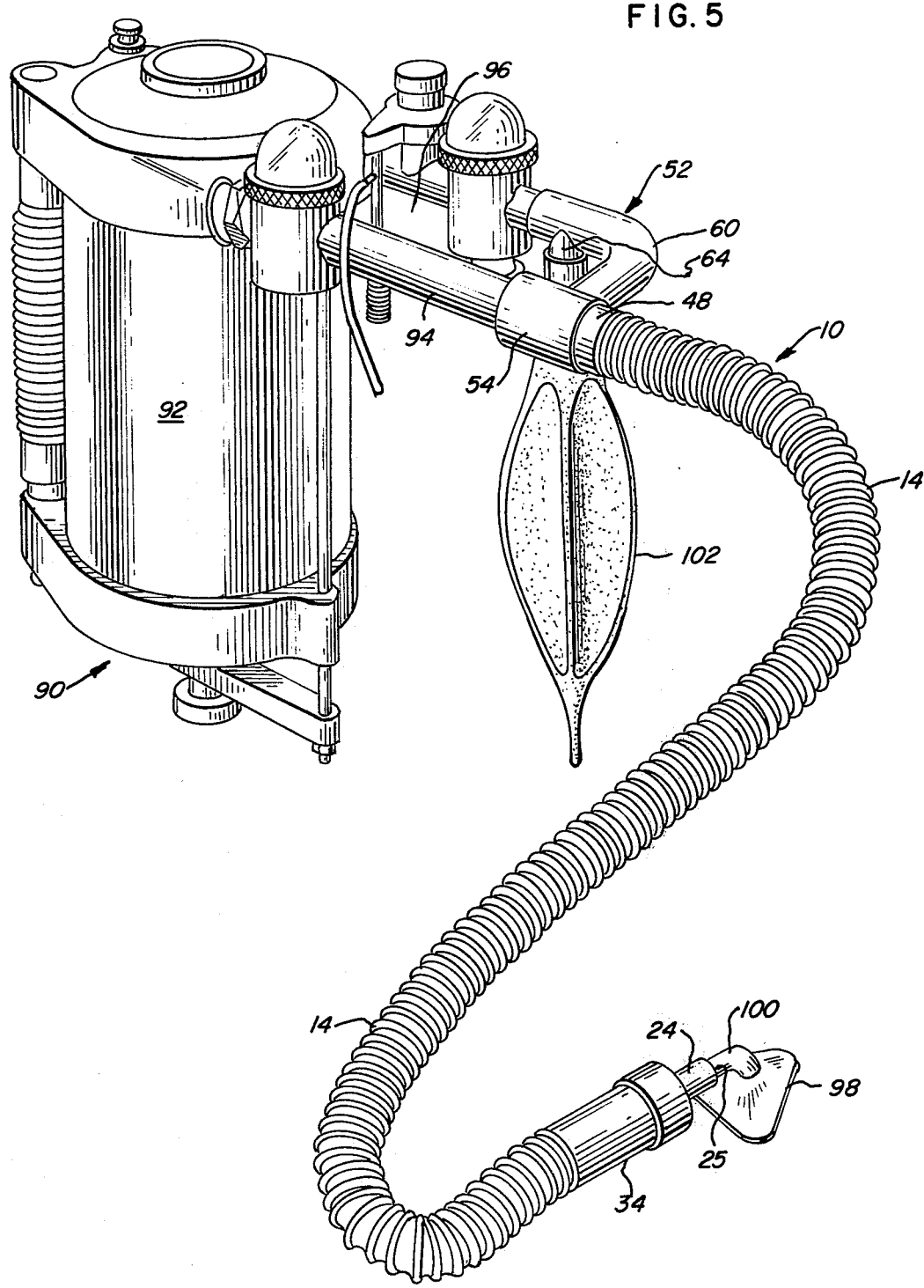

FIG. 4 is an elevational view, partly in cross section, showing a preferred embodiment of the invention wherein the tubular portions of the system are formed of smooth wall tubing, and FIG. 5 is a plan view showing the anesthesia breathing system of the present invention, showing the interconnection thereof with a patient face mask at one end and to a carbon dioxide absorber at the opposed end utilizing the U-shaped adaptor for interconnection to the existing equipment.

Referring now to the details of the drawings as depicted in FIGS. 1 through 4 of the drawings, the structure of the present invention is illustrated.

Figure 1:
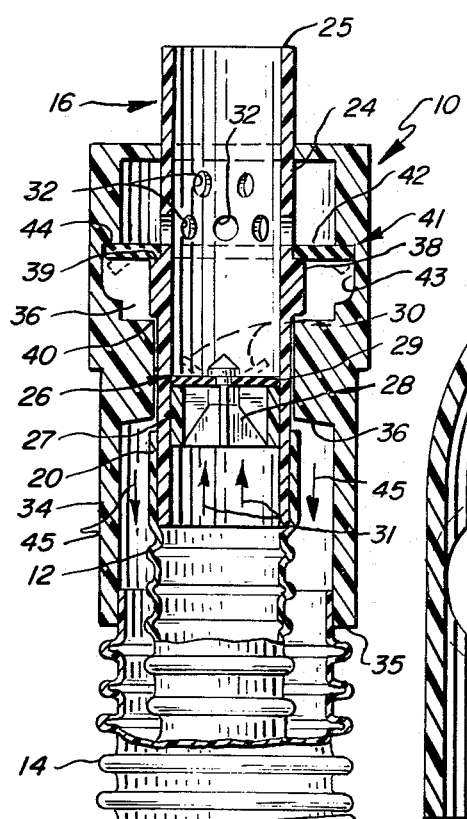
FIG. 1 is a side elevational view, partly in cross section and partly broken away, of the anesthesia breathing tubular system of the present invention.

FIG. 1 is a side elevational cross-sectional view partly broken away, showing the concentrically oriented tubing of the present invention. The circuit, generally referred to by the numeral 10, is shown to comprise an inner convoluted gas tube 12, and an outer convoluted gas tube 14. As will be seen in FIGS. 1, 2 and 4 of the drawings, the inner gas tube 12 is of a diameter substantially smaller than the outer gas tube 14, such that the inner tube 12, easily fits within the outer tube 14 and in concentric orientation and leaves a sufficiently large space between the respective walls thereof such as to permit gas flow through the space between the concentrically oriented tubes 12 and 14 respectively.

Figure 2:
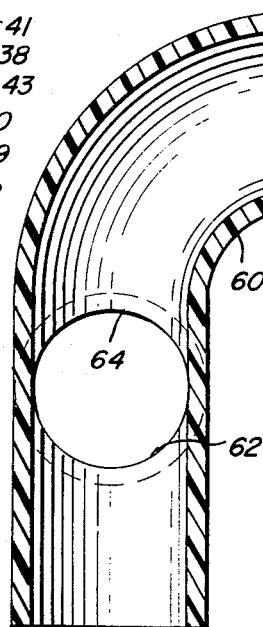
FIG. 2 is a side cross-section view showing the construction of the U-shaped adaptor and interconnection thereof with the tubing system into the present invention.

In this embodiment of the invention, the tubing is convoluted as shown in FIGS. 1 and 2 of the drawings to permit flexion while at the same time maintaining stability. Again as shown in FIG. 1 of the drawings, the circuit 10 terminates in a patient receiving end 16 and a gas source 18, at its opposed end.

It is observed that the inner gas tube 12 is convoluted, as indicated previously, and terminates in a patient end 20, spaced slightly rearwardly of the patient receiving end 16 of the circuit, and at the opposed end, terminates in a gas end 22, spaced slightly rearwardly of the gas source end 18 of the circuit. At the patient end 20, of the inner gas tube 12, is positioned a tube fitting 24, fixedly secured along the interior walls of the patient end 20, extending outwardly therefrom to a terminal end 25, which is fitted within a patient gas mask, or other patient supported inhalation-exhalation means. The tube fitting 24 is provided with a valve member 26, which includes a circular collar 27 and a frusto-conical support member 28. The upper circular edge of the collar 27 provides a valve seat for a flexible diaphragm 29 which is positioned across the circular collar 27. The frusto-conical support member provides structural rigidity for the valve and especially the flexible diaphragm 29, as well as to position the flexible diaphragm 29 with regard to the valve member 26 generally. From a view of FIG. 1 of the drawings, the operation of the valve member 26 is illustrated. As gas flows in the direction of the arrows 31 within the inner gas tube 12, the flexible diaphragm 29 is circumferentially moved away from the valve seat formed by the upper lip of the circular collar 27 into the position shown in the dotted lines 30 of FIG. 1. In this position, the valve member 26 is open to permit inhalation gas to enter through the inner gas tube 12 and hence, through the tube fitting 24, and thence into the patient face mask or other patient supported inhalation-exhalation device. During the expiration cycle, as gas attempts to pass down through the inner gas tube 12, the pressure of the gas will force the flexible membrane 29 against the valve seat formed by the upper lip of the circular collar 27 thereby closing the unidirectional valve member 26 such that the only exit for the exhaled gas is through the apertures 32 provided in the tube fitting 24 as will be more fully described hereinafter. In any event, it is quite apparent that the valve member 26 functions to prevent exhaled gas from flowing back into the inhalation tube 12, thereby to prevent gas cross-contamination.

As indicated above, the tube fitting 24 is provided with a plurality of apertures 32, which permit exhaled gases to flow through the apertures 32 of the tube fitting 24, into the exterior environment thereof, thereby to aid in the exhaustion of the exhaled gases from the patient, in a manner to be more fully described hereinafter.

The tube fitting 24 is securely held within an outer sleeve 34, having a lower end 35, which is fitted about and fixedly secured to the terminal end of the outer gas tube 14 as illustrated in FIG. 1. The construction of the interior portion of the outer sleeve 34 is designed to cooperate with the configuration of the tube fitting 24, such that the two elements are constructionally fixed one with respect to the other.

As illustrated in FIG. 1 of the drawings, the interior portion of the outer sleeve 34 is shown to be provided with a plurality of spacers 36, extending inwardly from the interior side walls thereof, and bearing against a portion of the tube fitting 24. Positioned immediately above the spacers 36, and forming a part of the tube fitting 24 is a circumferential ring 38 formed as a part of the exterior wall surfaces of the tube fitting 24. The circumferential ring 38 includes an upper bearing shoulder 39 and a lower abutting shoulder 40, respectively. The lower abutting shoulder 40 cooperates with the spacers 36 thereby to form a stop position for the tube fitting 24 with respect to the outer sleeve 34.

The second unidirectional valve member 41 is shown to consist of a flexible diaphragm 42 which is circumferentially disposed about the tube fitting 24 and bears upon the bearing shoulder 39 of the circumferential ring 38. The outer sleeve 34 is channeled as shown at 43 circumferentially such that a valve seat shoulder 44 is created and provides a seat against which the flexible membrane 42 may rest against when in the closed position. Hence, when gas exits through the apertures 32 of the tube fitting 24 and causes a positive pressure against the flexible membrane 42, the membrane 42 will move circumferentially into the position shown by the dotted lines in FIG. 1. In this posture, the valve member is then opened and exhaled gases may then pass into the outer gas tube 14 and travel the length thereof to the carbon dioxide absorber or the like.

The operation of the two undirectional valve members is now clearly apparent. As inhalation gas travels in the direction of the arrows 31 down the inner gas tube 12, the positive pressure against the back wall of the flexible diaphragm 29 forces that diaphragm 29 into the open position as illustrated by the dotted lines 30. The inhaled gas may then traverse the balance of the tube fitting 24 and enters the patient through a face mask or other such means. During the expiration cycle, exhaled gases will once again flow into the tube fitting 24 but due to the pressure caused against the flexible diaphragm 29, the diaphragm 29 will be forced against the circular collar 27 forming a seal and causing the exhaled gas to back up. As the exhaled gases back up, they will flow through the apertures 32 provided in the tube fitting 24 and commence building pressure immediately above the flexible diaphragm 42 of the second unidirectional valve member 41. As this pressure builds, the flexible diaphragm 42 will now be moved circumferentially away from the valve seat 44, thereby permitting the exhaled gases to travel in the direction of the arrows 45 into the outer gas tube 14 and hence, ultimately, into a carbon dioxide absorber or other device connected to the system for accepting exhaled gases.

The gas source end 18 of the circuit 10 is also illustrated in FIG. 1 of the drawings. It will be noted that the gas end 22 of the inner gas tube 12 is also provided with a lower tube fitting 46 which is fixedly secured along the interior portion of the gas end, of the tube 12 and extends outwardly therefrom. The outer gas tube 14 is similarly provided with a lower outer sleeve 48, fixedly secured along the outer walls of the outer gas tube 14, and extending downwardly therefrom, and surrounding the lower tube fitting 46 while at the same time providing a sufficient air space between the lower tube fitting 46 and lower outer sleeve 48, in order to permit gas flow therebetween. The interior surface of the cylindrical tube 54, to be described hereinafter is provided with a circumferential stop flange 49 which limits the travel of the lower outer sleeve 48 with respect to the cylindrical tube 54. Once again, the lower outer sleeve 48 is provided with a plurality of lower spacer members 50, which are formed as part of the interior surface of the lower outer sleeve 48 and extend inwardly therefrom abutting up against the outer walls of the lower tube fitting 46, thereby to maintain and stabilize the circuit generally, and to maintain a fixed relationship between the lower tube fitting 46 and lower outer sleeve 48. Hence, the spacers 36 provided at the forward end of the circuit 10, and the spacer members 50 provided at the lower end of the circuit 10 cooperate to maintain the inner gas tube 12 and outer gas tube 14, in fixed spacial relationship, thereby to provide air space, or gas space, between the respective tubes and hence, to permit gas flow in one direction within the inner gas tube 12, in the direction of the arrows 31, and to permit gas flow between the inner gas tube 12 and the outer gas tube 14, in the direction of the arrows 45. The advantages of this construction will be more fully explained hereinafter.

With specific reference to FIG. 2 of the drawings, the gas source end 18 is shown to be provided with a U-shaped adaptor 52, which permits the interconnection of the circuit 10 of the present invention to existing gas source equipment, in the manner illustrated in FIG. 5 of the drawings. The U-shaped adaptor 52 is formed by a cylindrical tube 54, having an upper connection end 55, which slides over and substantially frictionally engages the lower outer sleeve 48, by being slidably mounted thereabout. The lower portion of the cylindrical tube 54 is formed by a bottom wall 56, having a central aperture 57, therein, the diameter of the central aperture 57, being slightly larger than the outer diameter of the lower tube fitting 46. The construction of the cylindrical tube 54 is completed by lower connection tube 58, which partially surrounds the terminal end of the lower tube fitting 46 as shown in FIG. 2 of the drawings, and extends downwardly therefrom thereby to provide a connecting tube for interconnection with gas supply equipment.

The cylindrical tube 54 also includes a curvilinear arm 60 which extends laterally and downwardly outwardly therefrom the function of the curvilinear arm 60 being to provide another interconnection point with existing gas supply equipment. An aperture 62 provided in the arm 60, having a peripheral skirt 64 (FIG. 5) extending downwardly therefrom, the peripheral skirt 64 providing a mounting point for mounting a breathing bag in frictional relationship therewith, all as illustrated in FIG. 5 of the drawings. Hence, the adaptor 52 is shown to consist of the cylindrical tube 54, and the curvilinear arm 60, extending laterally and outwardly therefrom and provides means for adapting the circuit 10 of the present invention to existing equipment.

Figure 3:
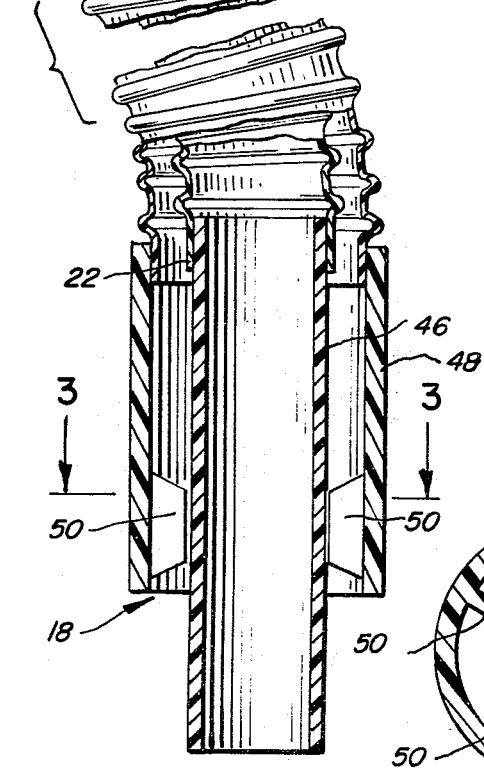
FIG. 3 is a cross sectional view illustrating the spacial relationship as between the outer and interior tubes and being held in spaced and fixed relation by means of a plurality of spacer member, all taken along the line 3—3 in FIG. 1.
Figure 3:
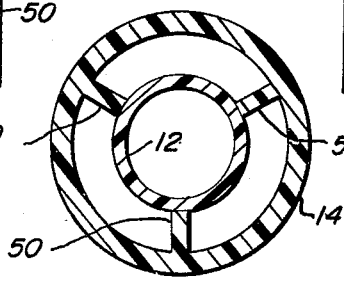

FIG. 3 of the drawings illustrates the structural relationship between the inner gas tube 12 and the outer gas tube 14, and the means by which the tubes 12 and 14 respectively are held in spaced relationship by means of the lower spacer members 50. Once again, by providing spacer members at least at one end of the circuit 10, and at the opposed end of the circuit 10, the spaced and fixed relationship between the concentrically oriented tubes 12 and 14 respectively, is maintained.

With reference to FIG. 4 of the drawings, an alternate embodiment of the present invention is illustrated. There is provided a circuit 70, including an inner gas tube 72 and an outer gas tube 74, FIG. 4 illustrating merely the gas source end 76 of the circuit. Once again, the inner gas tube 72 is provided with a lower tube fitting 78, fitted within the interior walls of the tube 72, and extending downwardly therefrom while the outer gas tube 74 is also provided with a lower outer sleeve 80, fitted about the outer walls of the outer gas tube 74 and extending downwardly therefrom and surrounding the tube fitting 78. The inner gas tube 72 and outer gas tube 74 are held in spaced and fixed relationship by means of the lower spacer members 82, as well as upper spacer members (not shown) in the same manner as described with respect to the embodiment shown in FIG. 1 of the drawings.

It will be observed that the concentrically oriented inner and outer gas tubes 72 and 74 respectively are smooth walled tubes and are considered to be an ideal embodiment of the invention. The differences between having convoluted tubes of the type shown in FIG. 1 of the drawings, as opposed to smooth wall tubes, as shown in FIG. 4 of the drawings, will be more fully explained hereinafter. It will also be noted that the inner gas tube 72, is provided with a helically wound wire 84, the wire 84 providing stability and strength for the inner gas tube 72, along its entire length.

With reference to FIG. 5 of the drawings, the anesthesia breathing circuit 10 of the present invention is illustrated as connected to an anesthetic gas supply system generally represented by the numeral 90. The gas supply system 90, generally includes an absorber 92, for absorbing carbon dioxide gas, an inhalation portion 94, for introducing gases into the circuit 10, for inhalation by the patient, and an exhalation portion 96, to receive exhaled gases from the patient and conduct the same to the absorber 92. In this type of system, portions of the exhaled gases, after absorption of the carbon dioxide in the absorber are reintroduced into the inhalation stream, along with additional portions of anesthetic gases and oxygen and reintroduced into the inhalation line for inhalation by the patient. As is shown in FIG. 5, the U-shaped adaptor 52, permits the interconnection of the circuit 10 of the present invention to existing equipment of the type represented by the numeral 90. The lower tube fitting 46, connects with the inhalation portion 94, of the gas supply system 90, while the curvilinear arm 60 of the U-shaped adaptor 52, connects with the exhalation portion 96 of the gas supply system 90, thereby to achieve connection of the circuit 10 to existing equipment. Since the lower tube fitting 46 establishes fluid communication with the inner gas tube 12, clearly gas supplied by the inhalation portion 94 of the equipment, will find its way through the inner gas tube 12, through the tubing connector 100, and to the patient face mask 98. It is apparent that the face mask 98 is connected to the upper tube fitting 24 and hence, gases flowing through the inner gas tube 12 will find their way to the patient. Similarly, exhaled gases are expelled through the tube connector 100 which interconnects the face mask 98 with the tube fitting 24. Exhaled gases will find their way into the tube fitting 24, but in view of the positioning of the unidirectional valve preventing flow of exhaled gas into inhalation tube 12, the exhaled gases will flow through the apertures 23, provided in the tube fitting 24, and hence, into the portion of the tubing between the inner gas tube 12 and the outer gas tube 14, by forcing the flexible diaphragm 42 of the second unidirectional valve member 41 into the open position, while concomitantly forcing the flexible diaphragm 29 of the first unidirectional valve member 26 into the closed position. The result is that one obtains counter-current gas flow with respect to the circuit 10 generally.

It will finally be noted that the U-shaped adaptor 52 also permits the use of a breathing bag 102 by interconnecting the same onto the peripheral skirt 64, immediately below the aperture 62 in the curvilinear arm 60.

In order to appreciate the advantages derived by an anesthetic breathing circuit 10 of the type described herein, it is perhaps necessary to consider various problems incident to such circuits and systems generally. As has been indicated previously, in presently available systems of this type, the unidirectional valves employed in the system are generally spaced and removed from a point adjacent to the point of inhalation or exhalation by patient.

The circuit of the present invention moves these valves to a point almost immediately adjacent the patient hence reducing the amount of dead space in the system. The difficulties observed in connection with dead space in the system is that the portion of the tubing circuit containing the dead space contains gases exhaled by the patient and cannot be swept out of the circuit very easily during each of the inhalation-exhalation cycles. As a result, the possibilities of gas contamination are greatly increased. The present invention, by reducing the amount of dead space to a small volume, that being the volume between the uni-directional valves and the point of patient inhalation-exhalation, permits virtually a complete sweeping of the circuit between each inahalation-exhalation cycle. In addition, the amount of exhaled gas which is reinhaled by the patient is substantially reduced.

With respect to the double concentrically oriented inhalation-exhalation tubes, a dual advantage is obtained by the construction as described herein. In the first place, as has been described, the exhaled gases exit through the circuit 10 in the space defined between the inner walls of the outer gas tube 14, and the outer walls defining the inner gas tube 12. On the other hand, inhaled gases are carried through the inner gas tube 12, directly to the patient. The result is that there is a counter-current gas flow of the inhaled vs. exhaled gases established, forming a heat exchanger such that the warmer exhaled gases flowing counter-currently with respect to the cooler inhaled gases tend to warm the inner gases during counter-current movement. In this manner, a very efficient system has been provided whereby the inhaled gases may be warmed throughout the entire path of travel of the gases, from the gas supply system to the patient, since heat will be exchanged from the warmer exhaled gases to the cooler inhaled gases across the tubular walls. It should be noted that, in most instances, the gases exhaled by patients is approximately 98°–99° F. and, as long as breathing continues, the exhaled gas will have a temperature of 25°–30° F. above the ambient atmosphere, and therefore, will continue to act as both an insulator and heat source for the inhaled gas, without any external or additional heat sources, by maintaining a uniform higher temperature in the inhalation tubing and less condensation of moisture in the inhaled gas will occur.

With additional moisture being supplied to the patient, less moisture will be taken from the mucosal membranes of the respiratory system. This is considered to be a desirable improvement by practitioners in the field.

Still another effect is achieved in that it has been observed that the exhaled gases have a tendency to give up heat at a portion of the circuit more closely adjacent to the patient, while picking up heat at a position more closely adjacent to the gas supply system. The result is that there is a more elevated temperature of the incoming gas as well as the outgoing gas, throughout the entire circuit, which again, is a function of having the exhaled gases act as an insulator, as well as providing the heat exchanger effect.

As has been described hereinabove, one embodiment of the invention contemplates corrugated tubing which has been found to be very flexible and yet quite stable and resistant to kinking. However, while such a system will operate within the scope and spirit of the present invention, it has been found that the corrugated wall surfaces of the tubing create gas turbulence as the gas flows and strikes the multi-faceted walls incident to corrugated tubing. In addition to gas turbulence it has been found that corrugated tubing provides many nesting points for bacterial growth along the breathing circuit, and since corrugated tubing is very difficult to wash and sterilize, the possibility of gas contamination by bacterial growth is ever present. Furthermore, should one attempt to wash and clean corrugated tubing, it is very difficult to dry the tubing, due once again, to the many surface areas which must be dried in order to ensure that the tubing is completely dried.

Another drawback incident to the corrugated type tubing resides in the fact that the increased surface area incident to such tubing results in additional heat loss since there is increased surface area. As such the gases will have a tendency to further cool as they traverse through the corrugated tubing. In addition, corrugated tubing tends to distend under pressure and this causes gas compression, which increases the resistance to exhalation. Smooth wall tubing on the other hand, minimizes heat loss by decreasing the surface area presented to the gas flow therethrough, and in addition, eliminates tube distension and thereby reduces the level of gas compression which results in less resistance to exhalation.

Hence, it is clear that corrugated tubing does present certain problems such as gas turbulence during the inhalation-exhalation cycle, nesting points for bacterial growth, and the possibility of incomplete drying of collected water vapor, and/or wash water, thereby further nurturing bacterial growth. To this end, there is provided an embodiment of the present invention which may be utilized with smooth wall tubing as depicted in FIG. 4 of the drawings, which still obtains all of the beneficial results indicated for the invention generally. As shown in FIG. 4 of the drawings, while applicant has provided a helically wound wire, denoted by the numeral 84, for stabilizing and maintaining the inner gas tube 72, it is proposed that with the proper type of plastic tubing, having sufficient rigidity while still permitting flexability, it is possible to eliminate the helically wound wire 84. In any event, the provision of smooth walled tubing of the type suggested herein, substantially minimizes gas turbulence, potential bacterial growth sites and simplifies the washing and drying operation of the tubing as well as decreasing the areas where water vapor may accumulate.

Finally, another advantage provided by the present invention is the provision of the U-shaped adaptor denoted by the numeral 52 which permits the interconnection of the tubing circuit of the present invention to be interconnected with existing equipment. In this manner, the anesthesia breathing circuit of the present invention may be incorporated with existing equipment, thereby obviating the necessity of modifying expensive gas supply and absorber systems presently available and in use, while still permitting the incorporation of the tubing circuit of the present invention. Furthermore, by providing an adaptor which is removable from the tubing circuit, as is permitted by the present invention, the tubing circuit may be disassembled by removing the adaptor and disconnecting the patient's face mask or endotracheal tube and permitting relative ease in terms of washing and sterilizing the tubing prior to each usage thereof. This feature also points out another advantage of the present invention in that the tubing may be used repeatedly while still permitting ease of cleaning to reduce and minimize the possibility of contamination or cross-contamination, while on the other hand, by selecting the proper type of plastic, a tubing circuit complying with the present invention may be made completely disposable. In addition, one may employ materials which are electroconductive to prevent the build-up of electrical charges on the patient relative to ground.

Another advantage obtained by the present invention resides in the minimizing of the amount of drag on the patient, since only one connection is made to a face mask or endotracheal tube. In presently available systems, it is necessary to have both an inhalation line and an exhalation line separately attached to a face mask, or the like, and this increases the amount of tubing to be contended with by the patient. The present invention permits but a single connection to be made, thereby minimizing the weight and inconvenience of having multiple tubes attached to the patient.

While there has been described what at present is considered to be the preferred embodiment of the invention, it will be understood that various modifications may be made therein and it is intended to cover in the appended claims all such modifications as fall within the true spirit and scope of the invention.

What is claimed is:

1. An anesthesia breathing system utilized in connection with systems for the administration of inhalation anesthetic agents, including a source of gas for inhalation positioned at one end of the system and patient-supported inhalation-exhalation means at the opposed end of the system, the improvement comprising in combination, a concentrically oriented double tubular inhalation-exhalation tube extending from one end of said system to the opposed end of said system and having one of said tubes positioned interiorly of the other of said tubes, one of said tubes carrying inhaled gas and the other of said tubes carrying exhaled gas, spacer means for supporting and maintaining said concentrically oriented tubes and spaced in relatively spacial relation, first unidirectional valve means mounted within said inhalation gas tube extending across the diametric dimension of said one of said tubes providing flow only in the direction from said one end of said system to said opposed end of said system and positioned adjacent the patient-supported inhalation-exhalation means for providing unidirectional gas flow therethrough, and second unidirectional valve means mounted within said exhalation gas tube and extending across the diametric dimension of the annular fluidic path between said concentric tubes for providing flow only in the direction from said opposed end of said system to said one end of said system and positioned adjacent the patient-supported inhalation-exhalation means for providing unidirectional gas flow therethrough, said first and second unidirectional valve means each comprising a valve seat and a flexible membrane seatable against said valve seat, said membrane allowing fluid to flow by flexure and movement of the membrane in one direction of applied fluidized pressure, and seatable against said valve seat thus not allowing flow when fluidized pressure is applied in the opposed direction, at least said inhalation line being formed of a flexible material rapidly permeable to heat transfer and the gas flow in said exhalation gas tube being countercurrent with respect to the gas flow in said inhalation gas tube, thereby to stabilize and maintain the temperature of the gas within said gas inhalation tube, without any extraneous source of heat, whereby gas suitable for patient inhalation enters said system through said inhalation tube and through said first unidirectional valve means to the patient while exhaled gas flows through said second unidirectional valve means in countercurrent relation with respect to the gas along said gas inhalation tube for exhaustion and/or purification from said system.

2. The anesthesia breathing system as set forth in claim 1, wherein each of said tubes presents a smooth outer and interior wall surface.

3. The anesthesia breathing system as set forth in claim 2 above wherein said ribs are positioned adjacent to at least the forward and rear portions of said double tubular system, to provide support and spacing relation at both ends of said system.

4. The anesthesia breathing system as set forth in claim 2 above, wherein said interior tube presents a smooth wall exteriorly and interiorly and further includes a wire helically wound thereabout to provide support for said interior tube.

5. The anesthesia breathing system as set forth in claim 1, wherein said spacer means comprises a plurality of circumferentially arranged ribs, extending inwardly from the interior wall of said outer tube, and in touching contact with the outer wall of said interior tube, thereby to space and maintain said outer and interior tubes in relatively fixed spacial relation.

6. The anesthesia breathing system as set forth in claim 1 above, which further includes adaptor means for interconnecting said system to a gas purification and absorption system.

7. The anesthesia breathing system as set forth in claim 6 above, wherein said adaptor means comprises a U-shaped sleeve member positionable about said outer tube and having one arm of said U-shaped tube in communication with said interior tube, and the other arm of said U-shaped tube in fluid communication with a sleeve surrounding said outer tube, such that the arm is in full communication with said outer tube.

8. The anesthesia breathing system as set forth in claim 7 above, wherein said arm in fluid communication with said outer tube further includes a breathing bag port, surrounded by an externally projecting collar to permit interconnection of a breathing bag in friction-engaging relation over said collar.

9. The anesthesia breathing system as set forth in claim 1 above, wherein each of said doubly oriented tubes are each convoluted to permit ease of flexion.

10. An anesthesia breathing system utilized in connection with systems for the administration of inhalation anesthetic agents, including a source of gas for inhalation positioned at one end of the system and patient supported inhalation-exhalation means at the opposed end of the system, the improvement comprising in combination, a concentrically oriented double tubular inhalation-exhalation line extending from one end of said system to the opposed end of said system and having one of said tubes positioned interiorly of the other of said tubes, one of said tubes carrying inhaled gas and the other of said tubes carrying exhaled gas, spacer means for supporting and maintaining said concentrically oriented tubes in spaced and relatively fixed spacial relation, first unidirectional valve means mounted within said inhalation gas tube extending across the diametric dimension of said one of said tubes providing flow only in the direction from said one end of said system to said opposed end of said system and positioned adjacent the patient-supported inhalation-exhalation means for providing unidirectional gas flow therethrough, and second unidirectional valve means mounted within said exhalation gas tube and extending across the diametric dimension of the annular fluidic path between said concentric tubes for providing flow only in the direction from said opposed end of said system to said one end of said system and positioned adjacent the patient-supported inhalation-exhalation means for providing unidirectional gas flow therethrough, said first and second unidirectional valve means each comprising a valve seat and a flexible membrane seatable against said valve seat, said membrane allowing fluid to flow by flexure and movement of the membrane in one direction of applied fluidized pressure, and seatable against said valve seat thus not allowing flow when fluidized pressure is applied in the opposed direction, at least said inhalation line being formed of a flexible material rapidly permeable to heat transfer and the gas flow in said inhalation gas tube being countercurrent with respect to the gas flow in respect to said exhalation gas tube, thereby to stabilize and maintain the temperature of the gas within said gas inhalation tube, without any extraneous source of heat, each of said first and second unidirectional valve means being positioned adjacent the patient-supported inhalation-exhalation means, whereby gas suitable for patient inhalation enters said system through said inhalation gas tube and flows through said first uni-directional valve means into and through said patient-supported inhalation exhalation means, while exhaled gases flow through said patient-supported inhalation-exhalation means and through said second unidirectional valve means and hence, through said exhalation gas tube for exhaustion and purification from the system.

* * * * *